United States Patent [19]

Scheinhütte

[11] Patent Number: 5,371,584
[45] Date of Patent: Dec. 6, 1994

[54] APPARATUS FOR THE DETECTION OF CONTAMINANTS IN AN ELONGATED TEXTILE PRODUCT

[75] Inventor: Hans-Jürgen Scheinhütte, Schindellegi, Switzerland

[73] Assignee: Gebruder Loepfe AF, Kempten, Switzerland

[21] Appl. No.: 3,581

[22] Filed: Jan. 13, 1993

[30] Foreign Application Priority Data

Jan. 31, 1992 [CH] Switzerland ............ 283/92-4

[51] Int. Cl.⁵ .................................. G01B 9/02
[52] U.S. Cl. ................................ 356/238; 356/430
[58] Field of Search ............... 356/238, 429, 430; 250/562, 572

[56] References Cited

U.S. PATENT DOCUMENTS 4,739,176  4/1988  Allen et al. ................. 356/430

FOREIGN PATENT DOCUMENTS 0197763  4/1986  European Pat. Off. .
197763  10/1986  European Pat. Off. .
4021487  1/1992  Germany .
674379A5  5/1990  Switzerland .
WO9313407  7/1983  WIPO .
WO8905468  6/1989  WIPO .

*Primary Examiner*—Richard A. Rosenberger
*Assistant Examiner*—Russell C. Wolfe
*Attorney, Agent, or Firm*—Harness, Dickey & Pierce

[57] ABSTRACT

For the detection of contaminants, a yarn or a thread is led through a zone of measurement, which is formed as a flat slit in an optically transparent body. This transparent body has outer surfaces for diffusely or non-diffusely reflecting light back into the body. Light is led into the body from several sources of light, such that the yarn is diffusely illuminated from all sides. The sources of light are arranged and adjusted such that the brightness of the yarn detected by a sensor is equal to the brightness of the yarn's background field. In this way, the measurement becomes independent of the yarn's thickness. Due to the use of a flat slit for receiving the yarn, the yarn can be inserted into the zone of measurement by the same procedures as they are used in conventional yarn cleaners.

7 Claims, 2 Drawing Sheets

APPARATUS FOR THE DETECTION OF CONTAMINANTS IN AN ELONGATED TEXTILE PRODUCT

BACKGROUND OF THE INVENTION

1. Field of the Invention

The invention relates to an apparatus for the detection of contaminants in an elongated textile product, such as a yarn or a thread.

Before spinning, raw fibers, e.g. cotton fibers, are mechanically cleaned in carding machines, where many contaminants, such as fragments of cotton shells, can be removed. Still, it cannot be ruled out that smaller contaminants, e.g. foreign fibers, remain in the yarn. Therefore, additional cleaning is required for obtaining a yarn of high quality.

2. Description of the Prior Art

Several devices are known for detecting and removing yarn faults, such as too thick or too thin sections of yarn. These so-called yarn cleaners automatically cut away the respective sections of the yarn.

In recent time yarn manufacturers have been endeavoring to detect and control not only such thickness variations, but also contaminants in the yarn, especially those due to foreign fiber material.

Such a device is e.g. known from the European patent EP-0 197 763. Its principle of measurement is based on diffusely illuminating the yarn through opaque zones of material such that the yarn does not differ in brightness from its background and therefore becomes invisible for a light detector as long as it does not contain a contaminant. In this way the influence of the yarn thickness on the detector signal can be eliminated.

The solution described in the above patent has the disadvantage that the yarn cannot be inserted into the apparatus in a conventional way as it is done in known yarn cleaners. This is due to the fact that the yarn runs at the bottom of a channel with angular walls to prevent the entry of foreign light.

Such an apparatus can therefore not be used in combination with conventional yarn insertion devices.

SUMMARY OF THE INVENTION

Hence, it is a general object of the present invention to provide an apparatus of the above mentioned kind with an insertion slit that is compatible with conventional yarn cleaners.

In the present invention, in order to implement this and still further objects of the invention, which will become more apparent as the description proceeds, the yarn is not illuminated through opaque zones as described in EP-0 197 763 but via diffuse or non-diffuse reflection on reflecting outer surfaces of a clearly transparent measuring body. While in the apparatus of EP-0 197 763 only a narrowly limited zone of measurement is flooded with diffuse light, the inventive measuring body with its reflecting outer surfaces represents a considerably larger light flooded volume. Therefore, its zone of measurement can be larger. Furthermore, the loss of light through its slit is comparatively small. The position of the yarn can vary more, making it possible to run the yarn through an open, flat slit in the measuring body, as it is done in conventional yarn cleaners.

In the zone of measurement, which is flooded by diffuse light, each light absorbing contaminant on the yarn decreases the light intensity. This can be detected in a light sensor, which is arranged at this zone of measurement. For making the signal of this sensor essentially independent of the thickness of the yarn, light sources are arranged on both sides of the zone of measurement. These light sources are mutually adjusted such that the reflected brightness of an uncontaminated yarn detected by the sensor is equal to the brightness of the background adjacent to the yarn.

BRIEF DESCRIPTION OF THE DRAWINGS

The invention will be better understood an objects other than those set forth above will become apparent when consideration is given to the following detailed description thereof. Such description makes reference to the annexed drawings, wherein.

DESCRIPTION OF A PREFERRED EMBODIMENT

Figure 1:
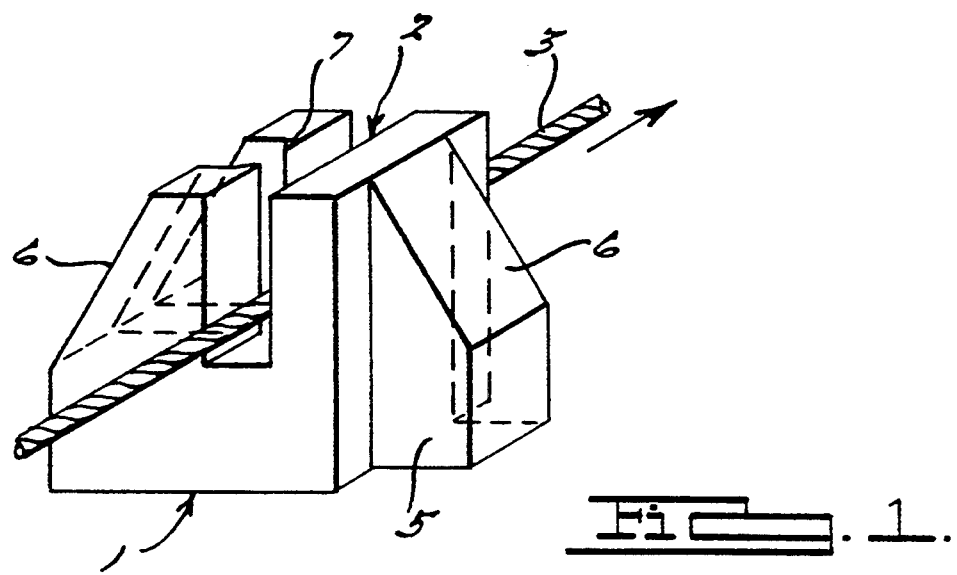
FIG. 1 shows an enlarged, perspective view of the measuring body of optically transparent material.
Figure 3:
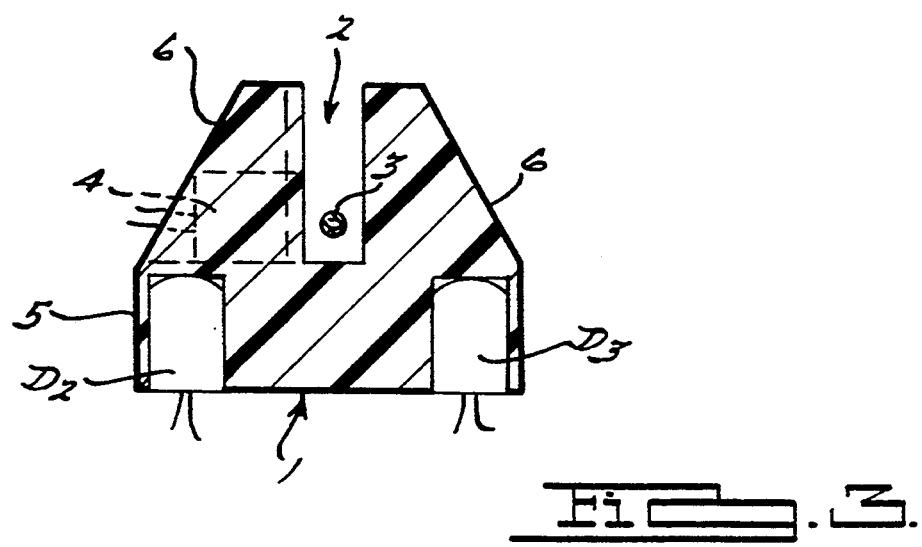
FIG. 3 is a sectional view along line III—III of FIG. 2.

As it can be seen from FIGS. 1 and 3, the detection apparatus comprises a measuring body 1 of a clearly transparent plastic material, preferably fabricated by injection moulding. This body contains a flat slit 2 for receiving the yarn to be examined. The slit 2, defining the zone of measurement, is also used as insertion aperture for the yarn, as it is usual in conventional yarn cleaners. The yarn is not fixed in the zone of measurement. It can move or even jump and change its position. Therefore, the zone of measurement is enlarged accordingly.

Figure 2:
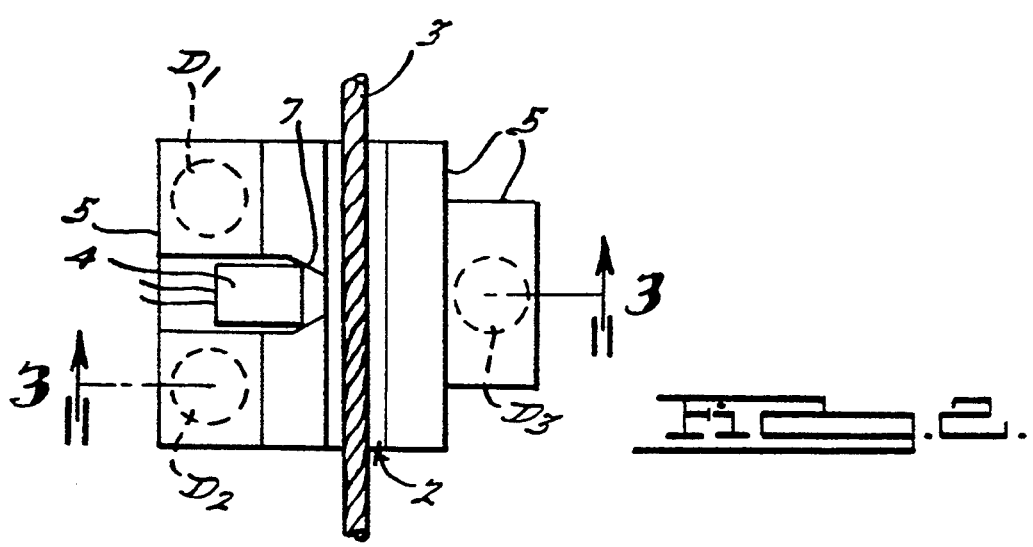
FIG. 2 is a top view of the body of FIG. 1.

As it can be seen in FIGS. 2 and 3, the zone of measurement receiving the yarn is limited on one side by the light sensor 4.

Three light emitting diodes $D_1$, $D_2$ and $D_3$ are arranged on the transparent body 1 for flooding it with light. Other sources of light, such as light guides, can also be used instead of the light emitting diodes. The body 1 is provided with diffusely or non-diffusely reflecting outer surfaces, which are e.g. coated by a mirror-like coating or a layer of reflecting paint 5. These surfaces reflect light into the body 1, such that a diffuse illumination results in the body 1 and especially in its zone of measurement.

For this purpose the body 1 comprises roof-like inclined surfaces 6 on its end opposite to the light diodes $D_1$, $D_2$ and $D_3$. Noses 7 are provided on both sides of the sensor 4, such that light emitted by the diodes $D_1$ and $D_2$ arrives obliquely on the sensor's side of the yarn. The third diode $D_3$ is arranged on the other side of the zone of measurement and is used for providing a background intensity for the sensor 4. This background intensity is set to be equal to the intensity of the light reflected from yarn 3 into the sensor 4. In this way, after appropriate adjustment, the uncontaminated yarn becomes virtually invisible for the sensor 4, such that the sensor signal is not affected by the thickness of the yarn.

Due to its mirrored surfaces, body 1 is completely flooded by light. Therefore, a dark fiber in a white yarn 3 leads to an error signal even if it is hidden from the sensor behind the yarn.

The apparatus is adjusted such that an uncontaminated yarn of arbitrary thickness centered in front of sensor 4 produces the same sensor signal as it is detected without a yarn. Hence, the amount of light detected by the sensor is equal with and without yarn.

Figure 4:
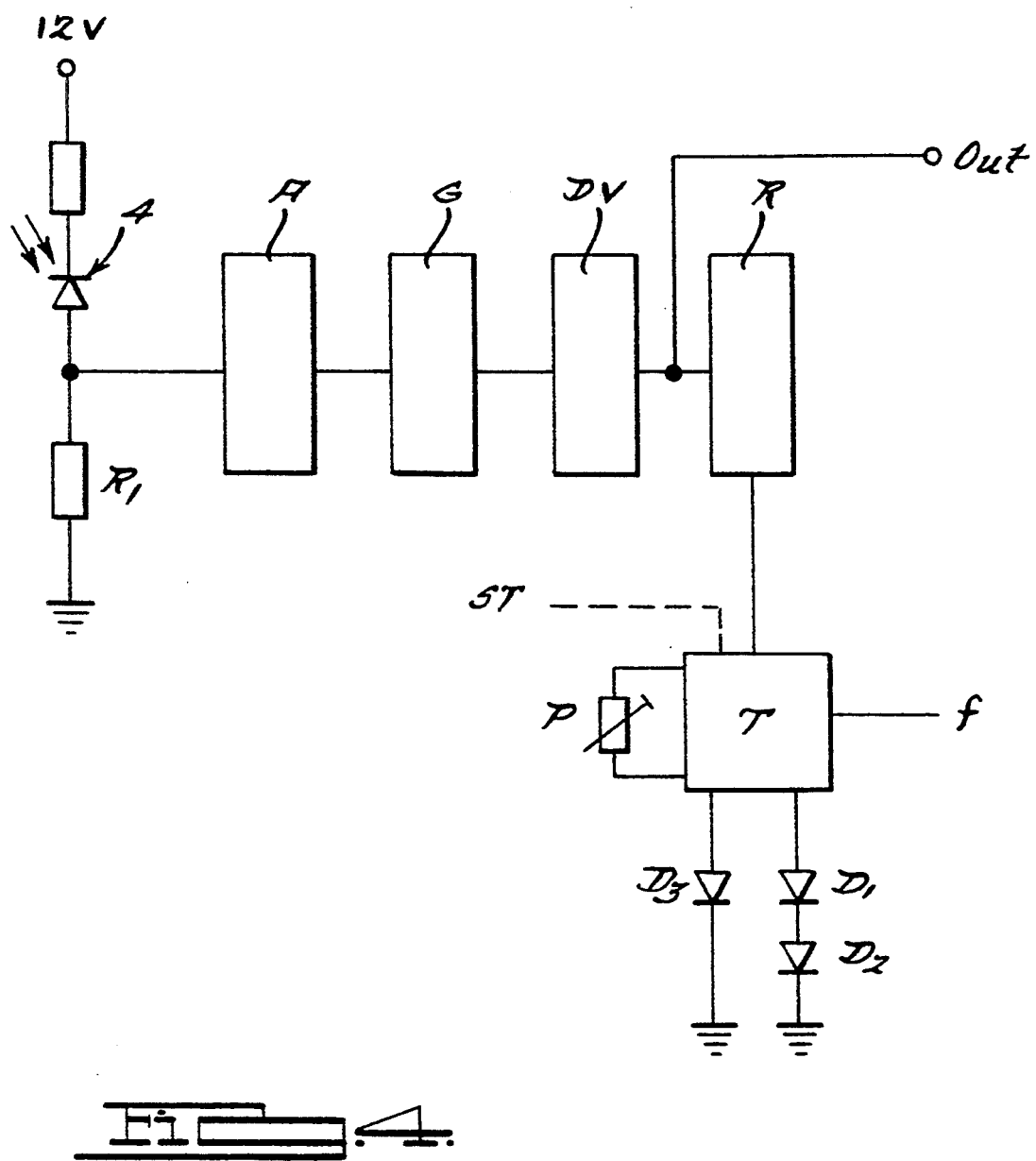
FIG. 4 is a partially schematic diagram of a control circuit of the apparatus.

FIG. 4 shows a schematic drawing of a circuit for controlling the apparatus. Pulsed light from the light emitting diodes $D_1$, $D_2$ and $D_3$ is received by the photodiode (sensor) 4 and leads to a rectangular voltage over the resistor $R_1$. This signal is amplified in an amplifier A. Its output voltage is rectified in a rectifier G and led to a second amplifier DV.

A decrease of the detected light intensity leads to a positive voltage at the output of the DC-amplifier DV. This voltage is also applied to a regulator R controlling the diodes $D_1$, $D_2$ and $D_3$. The positive voltage causes R to vary its output voltage until the signal at the output of the DC-amplifier DV goes back to zero.

For driving the diodes $D_1$, $D_2$ and $D_3$, a pulsed driver T is used, which is controlled by the regulator R. The diode $D_3$, which is used for defining the background brightness of the zone of measurement, can be adjusted by a potentiometer P and/or a control voltage ST.

The signal generated in the presence of contaminations at the output of the DC-amplifier DV is evaluated in a known kind of circuit for producing an error signal. The corresponding section of yarn is then cut away by a yarn cleaner. Since the inventive apparatus is provided with a conventional flat slit for receiving the yarn, the yarn can easily be reinserted after cutting.

While there is shown and described a present preferred embodiment of the invention, it is to be distinctly understood that the invention is not limited thereto, but may be otherwise variously embodied and practiced within the scope of the following claims.

I claim:

1. An apparatus for the detection of contaminants in an elongated textile product comprising
    a measuring body of an optically transparent material with inwardly reflecting outer surfaces and with a flat slit defining a zone of measurement, through which zone of measurement said textile product is led,
    at least one source of light for illuminating said measuring body, such that said textile product is illuminated essentially from all sides, and
    at least one light sensor arranged on a side of said zone of measurement,
    wherein the intensity of said at least one light source is adjusted such that the reflected brightness of said textile product detected by said light sensor in the absence of contaminants corresponds to the brightness of a background adjacent to said textile product in said zone of measurement.

2. The apparatus of claim 1, wherein said measuring body comprises outer inclined surfaces on both sides of said slit for reflecting light from said at least one source of light to said zone of measurement.

3. The apparatus of claim 2, wherein said at least one source of light is arranged on a side of said measuring body opposite to said inclined surfaces.

4. The apparatus of claim 1 comprising a plurality of said sources of light, wherein said sources of light are divided into two groups of light sources, wherein a first of said groups is provided essentially for generating light to be reflected from said textile product and to be detected by said light sensor, while a second of said groups is provided essentially for generating the brightness of said background adjacent to said textile product.

5. The apparatus of claim 4, wherein said first group of light sources is arranged on a first side of said slit and said second group of light sources is arranged on a second side of said slit.

6. The apparatus of claim 4, wherein said two groups of light sources are connected to a power supply, said power supply comprising adjustment means for varying a ratio of brightness of said two groups of light sources.

7. The apparatus of claim 1, wherein said at least one sensor and said at least one source of light are connected to a regulator circuit, which regulator circuit is adapted for adjusting the brightness of said at least one source of light such that in the absence of a contaminant an output signal of said apparatus is set to a predefined value.

* * * * *